(12) United States Patent
Wu et al.

(10) Patent No.: US 6,904,306 B1
(45) Date of Patent: Jun. 7, 2005

(54) METHOD AND APPARATUS FOR EVALUATION OF CONTRAST AGENT UPTAKE BASED ON DERIVED PARAMETRIC IMAGES

(75) Inventors: Dee H. Wu, Shaker Heights, OH (US); Sara M. Oberrecht, Cleveland, OH (US); Sara Hagey, Doylestown, OH (US); Agus Priatna, Waukesha, WI (US); David L. Foxall, Mentor, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 533 days.

(21) Appl. No.: 10/055,274

(22) Filed: Jan. 23, 2002

(51) Int. Cl.[7] .............................................. A61B 5/055
(52) U.S. Cl. ...................................... 600/420; 424/9.3
(58) Field of Search ................................ 600/410, 419, 600/420, 431, 481; 324/306, 309; 424/9.3; 382/128; 128/920, 922

(56) References Cited

U.S. PATENT DOCUMENTS

| 5,671,741 A | * | 9/1997 | Lang et al. ................. 600/415 |
| 6,687,527 B1 | * | 2/2004 | Wu et al. .................... 600/410 |
| 6,687,528 B2 | * | 2/2004 | Gupta et al. ................ 600/410 |
| 2003/0045791 A1 | * | 3/2003 | Carroll ........................ 600/419 |
| 2003/0211036 A1 | * | 11/2003 | Degani et al. ............. 424/1.11 |
| 2004/0127799 A1 | * | 7/2004 | Sorensen et al. ........... 600/481 |

FOREIGN PATENT DOCUMENTS

WO    WO 99/63355    * 12/1999    ........... G01R/33/54

OTHER PUBLICATIONS

Gorman, et al., "The Converging Squares Algorithm: An Efficient Method for Locating Peaks in Multidimensions", IEEE Trans. on Pattern Analysis and Machine Intelligence, vol. PAMI–6, No. 3, May 1984, pp. 280–288.
Wu, et al., "Myocardial Perfusion", Proc. Intl. Soc. Mag. Reson. Med 9 (2001).
Wilke, et al., "Magnetic Resonance First–Pass Myocardial Perfusion Imaging: Clinical Validation and Future Applications", J. Mag. Res. Imaging 10:676–685 (1999).
Wilke, et al., "Myocardial Perfusion Reserve: Assessment with Multisection, Quantitative, First–Pass MR Imaging", Radiology 1997: 204:373–384.
Wendland, et al., "Endogenous Susceptibility Contrast in Myocardium during Apnea Measured Using Gradient Recalled Echo Planar Imaging", MRM 29:273–276 (1993).
Li, et al., "Blood Oxygen Saturation Assessment In Vivo Using $T_2^*$ Estimation", MRM 39:685–690 (1998).
Priatna, et al., "Evaluation of Changes in Intrarenal Oxygenation in Rats Using Multiple Gradient–Recalled Echo (mGRE) Sequence", J. Mag. Res. Imaging 9:842–846 (1999).

(Continued)

Primary Examiner—Shawna J. Shaw
(74) Attorney, Agent, or Firm—Thomas M. Lundin

(57) ABSTRACT

A magnetic resonance imaging (MRI) apparatus (10) acquires a plurality of parametric images (60) with at least one varying imaging parameter. A parametric map (62) is constructed from the plurality of parametric images (60). At least one pilot parameter (64) is identified from at least the parametric map (62). The at least one identified pilot parameter (64) includes at least a volume of interest for a diagnostic image. A contrast agent (54) is administered to the patient (18). The identified volume of interest is imaged during influx of the administered contrast agent (54) into the identified volume of interest. The imaging uses the at least one identified pilot parameter (64).

28 Claims, 4 Drawing Sheets

OTHER PUBLICATIONS

Wendland, et al., "Contrast–Enhanced MRI for Quantification of Myocardial Viability", J. Mag. Res. Imaging 10:694–702 (1999).

Niemi, et al., "Myocardial Intensity Changes Associated with Flow Stimulation in Blood Oxygenation Sensitive Magnetic Resonance Imaging", MRM 36:78–82 (1996).

Simonetti, et al., "An Improved MR Imaging Technique for the Visualization of Myocardial Infarction", Radiology 2001: 218:215–223.

Beache, et al., "Imaging Perfusion Deficits in Ischemic Heart Disease with Susceptibility–Enhanced $T_2$–Weighted MRI: Preliminary Human Studies", Magnetic Resonance Imaging, vol. 16, No. 1, pp. 19–27 (1998).

Sechtem, et al., "Stress Functional MRI: Detection of Ischemic Heart, Disease and Myocardial Viability", J. Mag. Res. Imaging 10:667–675 (1999).

Lombardi, et al. "Relationship Between Function and Perfusion Early After Acute Myocardial Infarction", The Int'l Jour. Of Cardiovascular Imaging, vol. 17, No. 5, 2001, pp 383–393 XP008025105.

Zavaljevski, et al., "Multilevel Computed Hemodynamic Parameter Maps From Dynamic Perfusion MRI", IEEE Trans. On Instrumentation and Measurement, IEEE Inc. NY, US, vol. 48, No. 3, Jun. 1999, pp. 711–720 XP000920422.

Kiselev "On the Theoretical Basis of Perfusion Measurements by Dynamic Susceptibility Contrast MRI", Mag. Resonance in Medicine, vol. 46, 2001 pp. 1113–1122, XP002263348.

Strecker, et al., "Fast Functional MRA Using Time–Resolved Projection MR Angiography with Correlation Analysis", Mag. Resonance in Medicine, vol. 48, 2000, pp. 303–309, XP002263349.

* cited by examiner

METHOD AND APPARATUS FOR EVALUATION OF CONTRAST AGENT UPTAKE BASED ON DERIVED PARAMETRIC IMAGES

BACKGROUND OF THE INVENTION

The present invention relates to the medical imaging arts. It particularly relates to the assessment by magnetic resonance imaging (MRI) of coronary disease, heart tissue viability, and cardiac function, and will be described with particular reference thereto. However, the invention will also find application in other contrast-enhanced MRI imaging of various organs, such as the kidney, brain, and liver, as well as in other imaging modalities such as computed tomography (CT).

It is well known that cardiac diseases are a leading health problem in the United States at the present time. Myocardial infarctions, popularly known as heart attacks, are a leading cause of death. However, in spite of its prevalence, diagnosis is inconsistent. More than half of the individuals who die of a heart attack do not exhibit previously recorded symptoms.

Although often undiagnosed, many catastrophic myocardial infarctions are preceded by a prolonged period of incipient coronary disease in the form of partial blockages of the smaller coronary vessels. The incipient forms of cardiac disease can produce chest pains, excessive weariness, and other symptoms which usually only manifest during periods of exercise or other strenuous exertion. These symptoms are often misdiagnosed as indigestion or other minor medical conditions. The incipient forms of coronary disease can also produce small-scale infarctions, popularly known as "silent heart attacks", that kill portions of the heart tissue without producing clear and unambiguous symptoms.

In the early stages, the incipient forms of coronary disease are often controllable and sometimes even completely reversible, through the use of dietary and lifestyle changes or by relatively minor medical procedures such as coronary stent implantation or vascular catheterization treatments. Conversely, if left untreated the incipient forms often develop into more serious coronary diseases that lead to major heart attacks or other life threatening medical conditions. Hence, early diagnosis of incipient coronary disease is critical.

One reason why medical personnel frequently miss the early signs of incipient coronary disease is a dearth of convenient and relatively inexpensive methods for unambiguous diagnosis. The early coronary vascular blockages typically occur in small blood vessels which do not resolve well in conventional medical imaging techniques such as magnetic resonance imaging (MRI) or multi-slice computed tomography (CT). The vessels involved are too small and too numerous to practically investigate using vascular catherization diagnostic techniques. Catheterization procedures are also expensive and carry a higher degree of medical risk, further reducing their attractiveness for diagnosing ambiguous cases.

An indirect method of detecting small coronary vessel blockages is through monitoring of the uptake of an applied contrast agent bolus by heart tissue. Poorly oxygenated or dead cardiac tissue is revealed in this technique by differences in contrast agent uptake. A number of medical imaging modalities have been employed for investigating myocardial function and tissue viability, including: single-photon emission computed tomography (SPECT), typically using Th-201 or Tc-99m radiopharmaceutical agents to measure relative tissue uptake rates; positron emission tomography (PET) using an 18-F (FDG) contrast agent; and echocardiography using low dose stress agents.

MRI has also been employed for investigating myocardial function and tissue viability. In a contrast-enhanced method using a magnetic contrast agent such as a gadolinium (Gd) chelate, the Gd is administered as a bolus injection and rapid MRI measurements of several slices are performed, focusing on the ventricular or apex portions of the heart which are most commonly first affected by coronary blockages, in the hope that poorly oxygenated or dead tissues resulting from coronary vessel blockages will be detected in the Gd-sensitive MRI images due to altered Gd uptake in the damaged tissues. This approach is known as a "first-pass method" (FPM). The clinician has only a few seconds to acquire imaging data, limited by the rapid uptake of Gd into the cardiac tissue. It is critical that the area imaged during this short time includes the cardiac region affected by the vascular blockage or blockages, and a failure to do so will typically result in a failed test and potentially incorrect medical diagnosis. Thus, it is desirable to acquire image slices that substantially cover the heart volume. However, because of the limited available imaging time, tradeoffs are made between the volume coverage and the resolution with the result that full imaging coverage of the entire heart with satisfactory resolution is seldom achievable in FPM.

Once the Gd is substantially absorbed, however, it typically takes on the order of tens of minutes to hours for the Gd agent to be fully removed from the blood by the kidneys. The slow removal of Gd from heart tissue makes it difficult to reliably repeat high-quality cardiac FPM imaging using more than one Gd bolus injection in a single imaging session due to residual contamination from previous Gd boluses. This makes it preferable to acquire good images using only a single Gd bolus injection.

In the past, the MRI operator attempting to acquire FPM images for evaluating myocardial function and tissue viability has had very limited prior knowledge about appropriate imaging conditions. The operator selects several (e.g., six or seven) relatively low-resolution slices, typically axially oriented and targeting in the apex region of the heart especially including the ventricles. Due to time constraints, a more complete spatial mapping of the heart, requiring on the order of nine slices to fully cover the entire heart with adequate slice resolution, is not practical during FPM imaging. Increased speed through the use of higher gradient-slew rates may not be permissible due to safety considerations. The slice selection is made without significant foreknowledge of the defect to be imaged, and so a strong possibility exists that the selected several slices will not optimally intersect the unknown defect.

A variation on FPM are the late or delayed enhancement methods, in which imaging is performed during a time when the Gd is removed from the heart tissue. Coronary tissues with reduced or blocked blood flow typically retain the Gd longer than well oxygenated tissues, resulting in "late" contrast enhancement. Late enhancement has the advantage of a much broader acquisition time frame, on the order of minutes, compared with FPM. However, the late enhancement contrast is quite weak, and well-tuned imaging conditions are important for accurate imaging. Furthermore, the delay between administering the Gd and subsequent removal by the kidneys is variable on the order of tens of minutes to hours. Such long and uncertain delays can be problematic in a clinical environment where the MRI facility is operated on a tight schedule.

Yet another MRI method for investigating myocardial function and tissue viability employs blood oxygenation level dependence (BOLD) contrast. BOLD contrast results from the magnetic properties of the hemoglobin molecule that carries oxygen in the blood. Blood hemoglobin exists in two forms: oxyhemoglobin, which carries oxygen; and deoxyhemoglobin, which does not carry oxygen. The two hemoglobin forms have different magnetic properties: oxyhemoglobin is a diamagnetic molecule, while deoxyhemoglobin is a paramagnetic molecule. This difference in magnetic properties due to the presence or absence of oxygen is detectable by the MRI apparatus, and BOLD contrast MRI images can be produced having contrast related to the ratio of the two hemoglobin types. Since vascular blockages affect transfer of oxygenated blood into tissue and removal of deoxygenated blood from the tissue, the BOLD contrast mechanism is useful for imaging tissue oxygenation.

The BOLD contrast is typically imaged using T2* or T2 weighted imaging. BOLD contrast has been exploited in brain imaging, where it is sometimes called functional MRI, and has also been employed in cardiac imaging to a limited extent. In typical BOLD cardiac imaging, a stress agent is administered to simulate a state of high exertion which enhances oxygen demands of the cardiac tissue, followed by BOLD contrast imaging. In some cases, concern for patient safety or other issues may preclude application of the stress agent.

The present invention contemplates an improved method and apparatus for the magnetic resonance imaging (MRI) of coronary disease, tissue viability, and cardiac function which overcomes the aforementioned limitations and others.

SUMMARY OF THE INVENTION

According to one aspect of the invention, a method is provided for imaging tissue viability or vascular function in a patient using a magnetic resonance imaging (MRI) apparatus. A parametric map is acquired having blood oxygenation level dependent contrast. Piloting information is determined, including at least a selected slice orientation, based on the blood oxygenation contrast of the parametric map. A magnetic contrast agent is administered to the patient. Imaging is performed during a transient distribution of the contrast agent in the patient using imaging parameters based on the piloting information.

According to another aspect of the invention, a method is provided for assessing tissue in a patient using a magnetic resonance imaging (MRI) apparatus. A plurality of parametric images are acquired with at least one varying imaging parameter. A parametric map is constructed from the plurality of parametric images. At least one pilot parameter is identified from at least the parametric map. The at least one identified pilot parameter includes at least a volume of interest for a diagnostic image. A contrast agent is administered to the patient. The identified volume of interest is imaged during influx of the administered contrast agent into the identified volume of interest. The imaging uses the at least one identified pilot parameter.

According to yet another aspect of the invention, an apparatus is disclosed for characterizing contrast agent uptake in a patient. A means is provided for exciting a selected magnetic resonance in the patient. A means is provided for detecting radio-frequency resonance signals emanating from the patient responsive to the exciting of the selected magnetic resonance. A means is provided for reconstructing image representations from the detected radio-frequency resonance signals. A means is provided for controlling the exciting means, the detecting means, and the reconstructing means. The means for controlling implements the steps of: acquiring a plurality of images of a region of interest in the patient wherein the plurality of images parametrically depend upon at least one imaging parameter; constructing a parametric map based on the plurality of images; determining optimized imaging conditions based on at least the parametric map; and first-pass imaging during an uptake of an administered contrast agent into the region of interest wherein the first-pass imaging includes contrast due to the administered contrast agent.

One advantage of the present invention is that it takes advantage of the complementary strengths of the BOLD and FPM imaging techniques to produce an improved clinical work flow.

Another advantage of the present invention resides in an optimization of slice positioning and orientation for transient contrast agent-enhanced imaging.

Another advantage of the present invention is that it provides for obtaining piloting information such as an optimized imaging region of interest, number of slices, slice location, slice orientation, slice thickness, imaging field of view, and the like, prior to performing time critical imaging of a transient contrast agent distribution in the optimized region of interest.

Another advantage of the present invention is that it maximizes the probability of acquiring high quality functional cardiac MRI images.

Yet another advantage of the present invention is that it makes optimally efficient use of limited clinical MRI facility time resources.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
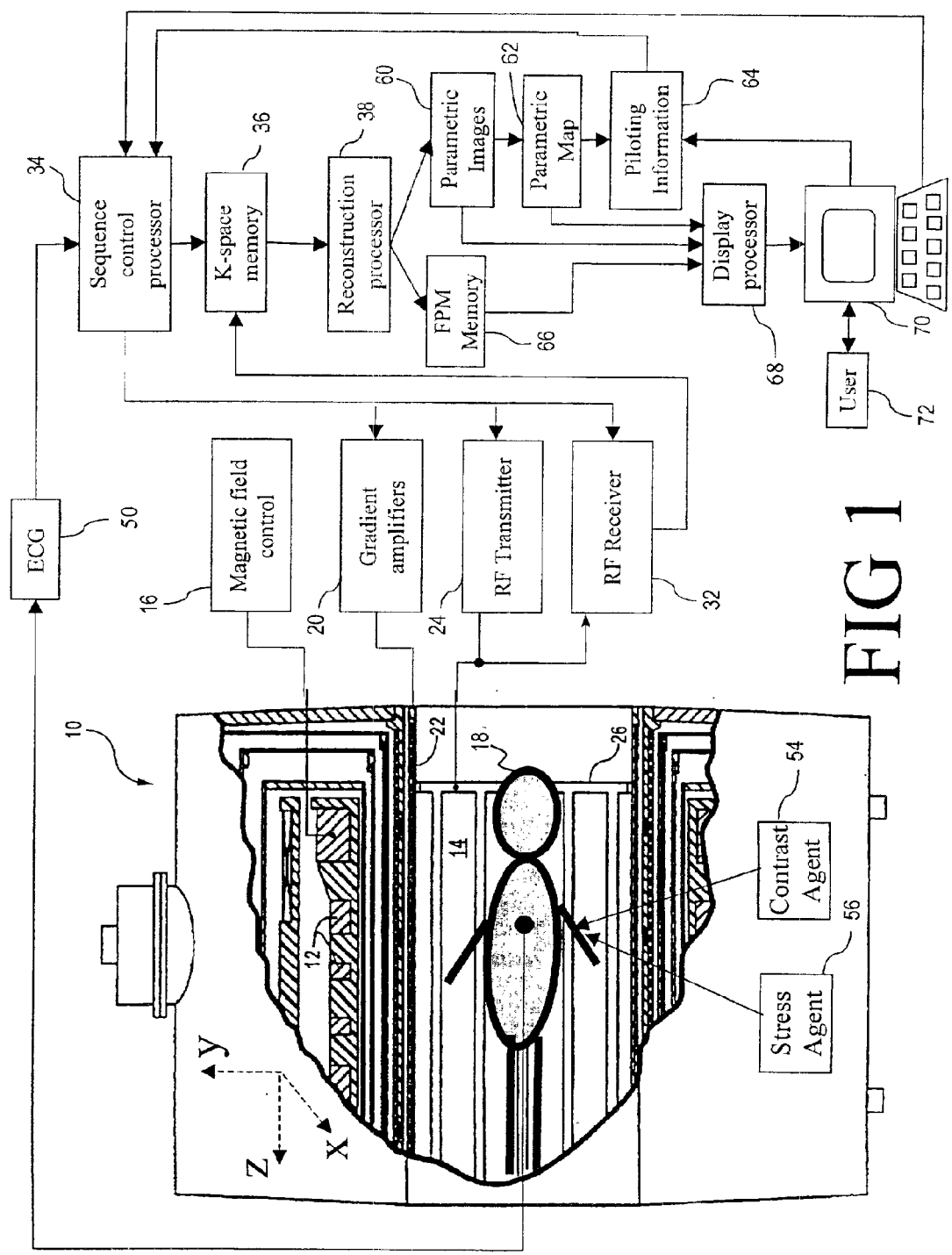
FIG. 1 is a schematic diagram of an exemplary magnetic resonance imaging (MRI) apparatus in accordance with the invention.

With reference to FIG. 1, a magnetic resonance imaging (MRI) scanner 10 includes superconducting or resistive magnets 12 that create a substantially uniform, temporally constant main magnetic field $B_0$ along a z-axis through an examination region 14. Although a bore-type magnet is illustrated in FIG. 1, the present invention is equally applicable to open magnet systems and other known types of MRI scanners. The magnets 12 are controlled by a main magnetic field control 16. Imaging is conducted by executing a magnetic resonance (MR) sequence with the subject being imaged, e.g. a patient 18, placed with his or her heart or other region of interest within the examination region 14. Typically, the region of interest is placed at the isocenter.

The magnetic resonance sequence entails a series of RF and magnetic field gradient pulses that are applied to the subject to invert or excite magnetic spins, induce magnetic resonance, refocus magnetic resonance, manipulate magnetic resonance, spatially and otherwise encode the magnetic resonance, saturate spins, and the like. More specifically, gradient pulse amplifiers 20 apply current pulses to a whole body gradient coil assembly 22 to create magnetic field gradients relative to x-, y-, and z-axes of the examination region 14.

An RF transmitter 24, preferably digital, applies RF pulses or pulse packets to a whole-body RF coil 26 to transmit RF pulses into the examination region. A typical RF pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region.

For whole-body applications, the resulting resonance signals, generated as a result of a selected manipulation, are also picked up by the whole-body RF coil 26. Alternately, for generating RF pulses in limited regions of the subject, local RF coils (not shown) are placed contiguous to the selected region. For example, as is known in the art, an insertable head coil or other such specialized RF coils may be employed. The RF system also optionally includes a phased array receive coil (not shown) whereby partial parallel imaging (PPI) techniques known to the art are enabled. In one embodiment, the whole-body RF coil 26 induces resonance and a local RF coil or coil array receives magnetic resonance signals emanating from the selected region. In other embodiments, the local RF coil both excites resonance and receives the resulting magnetic resonance signals.

Regardless of the RF coil configuration and the application thereof, the resultant RF magnetic resonance signals that are picked up by one or another of the RF coils is received and demodulated by an RF receiver 32, which is preferably a digital receiver. A sequence control processor 34 controls the gradient pulse amplifiers 20, the RF transmitter 24, and the RF receiver 32 to produce an integrated MRI pulse sequence and readout waveforms that generate the selected magnetic resonance (MR) signals and optional echoes, provide appropriate encoding gradients to spatially encode the resultant MR response, and coordinate MR pickup and receive operations.

The MRI sequence typically includes a complex series of magnetic field gradient pulses or sweeps generated by the gradient amplifiers 20 which along with selected RF pulses generated by RF coils 26 result in magnetic resonance echoes that map into k-space. The resultant magnetic resonance data is stored in a k-space memory 36. The k-space data is processed by a reconstruction processor 38, which is typically an inverse Fourier transform processor or other reconstruction processor known to the art, to produce a three-dimensional or multi-slice reconstructed image representation.

In cardiac imaging, the patient 18 is imaged by the MRI system 10 using imaging conditions that particularly emphasize the heart muscle, blood tissue, blood movement or flow, contrast agent uptake into cardiac tissues, or other aspect of clinical interest. To avoid blurring due to the motion of the pulsating heart, the cardiac cycle is advantageously monitored non-invasively using an electrocardiograph (ECG) 50. In the illustrated embodiment of FIG. 1, the ECG 50 is input to the sequence control processor 34, which monitors the ECG 50 signal for a pre-selected trigger event in the quasi-periodic electrocardiogram. Based on the trigger event and a knowledge of the relationship of the ECG signal to the cardiac cycle, the image acquisition is synchronized with a selected phase of the cardiac cycle. This synchronization approach is known in the art as prospective cardiac gating.

Those skilled in the art will recognize that other synchronization methods can be employed. For example, in retrospective cardiac gating the ECG 50 signal is recorded along with the MRI image acquisition. The recorded ECG 50 signal is referenced by the reconstruction processor 38 to select MRI data corresponding to a selected cardiac phase for image reconstruction. Other cardiac motion monitors are also contemplated such as navigator echoes, ultrasound, and the like. Cardiac segmented gated imaging, in which image data lines obtained over several cardiac cycles are combined to form a singular image, can be performed using either prospective or retrospective cardiac gating.

Appropriate imaging sequences are employed, which in one suitable embodiment include imaging having blood oxygenation level dependence (BOLD) contrast, imaging employing a first pass method (FPM), and late or delayed enhancement imaging. For the FPM or delayed enhancement imaging, a magnetic contrast agent 54 is administered to the patient 18 and the influx (FPM) or removal (late enhancement) of the contrast agent is monitored with respect to time. Contrast agents selected from the gadolinium or Dysprosium families of agents are often used for cardiac FPM and late enhancement imaging.

For any of BOLD, FPM, or delayed enhancement imaging, a stress agent 56 is optionally administered to the patient 18 to stress the patient 18 chemically. The stress agent 56 raises the metabolism of the patient 18, inducing the heart to work harder and demand more oxygen. Under such stressed conditions, regions of cardiac tissue which have poor communication with the coronary vascular system due to vessel blockages can become depleted of oxygenated blood. Similarly, tissues which have died due to past myocardial infarction events become more apparent due to the lack of oxygen absorption at the infarcted regions. Typical stress agents used in cardiac functional imaging include dobutamine, dipyridamole, and adenosine.

In one suitable embodiment, the sequence controller 34 initially implements parametric imaging sequences in the absence of the magnetic contrast agent 54. The parametric images are reconstructed and stored in a parametric images memory 60. The parametric images advantageously can be acquired over a relatively extended period of time compared with FPM imaging. If the stress agent 56 is used during the acquisition, the parametric imaging is coordinated with the time frame of the stress agent 56 application and effect. For typical stress agents 56 this time frame provides an imaging window at least of the order of minutes. Based on the stored parametric images 60, parametric map 62 is constructed.

In one suitable parametric mapping, the parametric images 60 include a plurality of images of a slice of the cardiac region using a varying T2* or T2 weighting. Such images can be acquired using a multiple-echo sequence incorporating several echo times. For each pixel of the slice, the T2* or T2 decay time constant (or the corresponding decay rate) is extracted by a regression analysis of the rate of pixel intensity decay at the several echo times, with the resultant T2* or T2 value at each pixel collectively forming the parametric map 62. A T2* or T2 parametric map includes blood oxygenation level dependent (BOLD) contrast, and is suitable for obtaining pilot information for FPM imaging of cardiac tissue damage related to coronary disease. The pilot information includes optimized imaging parameters for subsequent time-critical first pass method (FPM) imaging, and can include such things as a slice position and orientation, slice thickness, and other imaging parameters.

The sequence used to construct the T2 or T2* parametric mapping employs parametric imaging 60 echoes designed such that the parametric map image 62 is generated from samples collected at each individual echo time, with all samples taken from the same slice location. The pixel intensity over the several sampling echoes exhibits approximately exponential intensity decay, due to the T2* decay or another dominant resonance decay mechanism selected by the imaging conditions. The exponential decay can be modeled as:

$$x_i = be^{at_i} \quad (1),$$

where $t_i$ is the echo time of the ith sampling window, $x_i$ is the pixel intensity at time $t_i$, and the parameters a and b are to be obtained by regression analysis. The parameters a and b are obtained by regression analysis at each pixel, and a suitable parametric map is constructed by spatially plotting parameter a, parameter b, or a mathematical combination therof.

In an exemplary regression analysis, the parameters a and b are obtained by minimizing an error function E given by:

$$E = \sum_{i=1}^{N} (x_i - be^{at_i})^2, \quad (2)$$

where E is the error to be minimized by optimizing a and b, and N is the number of sampling images 60. The exponential function can be eliminated by taking the logarithm of equation (1):

$$\ln x_i = \ln b + at_i \quad (3),$$

to produce a linearized equation with respect to parameters a and ln b. The least squares figure of merit corresponding to equation (3) is:

$$E = \sum_{i=1}^{N} (\ln x_i - (\ln b + at_i))^2, \quad (4)$$

Taking the partial derivatives with respect to parameters a and ln b yields normal equations of the form:

$$0 = \frac{\partial}{\partial a} \sum_{i=1}^{N} (\ln x_i - (\ln b + at_i))^2 \quad (5)$$

$$0 = \frac{\partial}{\partial (\ln b)} \sum_{i=1}^{N} (\ln x_i - (\ln b + at_i))^2,$$

which can be rewritten as:

$$0 = 2 \sum_{i=1}^{N} (\ln x_i - (\ln b + at_i))(-t_i) \quad (6)$$

$$0 = 2 \sum_{i=1}^{N} (\ln x_i - (\ln b + at_i))(-1).$$

The equations (6) are linear, and an exact solution corresponding to the minimized error E is given by:

$$a = \frac{N \sum_{i=1}^{N} t_i \ln x_i - \sum_{i=1}^{N} t_i \sum_{i=1}^{N} \ln x_i}{N \sum_{i=1}^{N} t_i^2 - \left(\sum_{i=1}^{N} t_i\right)^2} \quad (7)$$

$$\ln b = \frac{\sum_{i=1}^{N} t_i^2 \sum_{i=1}^{N} \ln x_i - \sum_{i=1}^{N} (t_i \ln x_i) \sum_{i=1}^{N} t_i}{N \sum_{i=1}^{N} t_i^2 - \left(\sum_{i=1}^{N} t_i\right)^2}.$$

Equation (7) is evaluated for each pixel, and the pixel-by-pixel results are combined to form the parametric map 62. The parametric map 62 is constructed by spatially plotting a, ln b, or b, for example.

For imaging with low signal-to-noise ratios, the construction of a BOLD parametric map using exponential regression of multiple-echo images having varying T2* or T2 weightings as described above is sometimes impractical due to noise interference. In another parametric mapping embodiment particularly suitable for lower signal-to-noise ratio imaging (although not restricted thereto), a t-test known to the art is employed. T2* or T2 weighted imaging is first performed without the stress agent 56 to obtain $N_o$ images of the unstressed cardiac tissue. The stress agent 56 is then administered, and $N_s$ images of the stressed cardiac tissue are acquired. A suitable number of unstressed and stressed images is typically about five to ten images each, with more images preferred for lower signal-to-noise ratios. After employing suitable image processing or filtering and image registration known to the art, the parametric map 62 is constructed by calculating a t-test for each pixel according to:

$$t = \frac{\mu_s - \mu_o}{\sqrt{\frac{\sigma_s^2}{N_s} + \frac{\sigma_o^2}{N_o}}}, \quad (8)$$

where $\mu_s$ and $\mu_o$ are the stressed and unstressed mean pixel values, respectively, given by:

$$\mu_s = \sum_{n=1}^{N_s} \frac{x_{s,n}}{N_s}, \quad \mu_o = \sum_{m=1}^{N_o} \frac{x_{o,m}}{N_o}, \quad (9)$$

and $\sigma_s$ and $\sigma_o$ are the stressed and unstressed pixel variance values, respectively, given by:

$$\sigma_s^2 = \frac{\left(\sum_{n=1}^{N_s} x_{s,n}^2\right) - \frac{1}{N_s}\left(\sum_{n=1}^{N_s} x_{s,n}\right)^2}{N_s - 1}, \sigma_s^2 = \frac{\left(\sum_{m=1}^{N_s} x_{o,m}^2\right) - \frac{1}{N_o}\left(\sum_{m=1}^{N_o} x_{o,m}\right)^2}{N_o - 1}, \quad (10)$$

and $x_{s,n}$ and $x_{o,m}$ are the stressed and unstressed pixel values, respectively. The t-test value calculated for each pixel collectively forms the parametric map, which has BOLD contrast due to the T2* or T2 weighting.

Equation (8) is appropriate for imaging where the stress generally increases the pixel intensity. For imaging where the stress generally decreases the pixel intensity, equation (8) is suitably rewritten as:

$$t = \frac{\mu_o - \mu_s}{\sqrt{\frac{\sigma_s^2}{N_s} + \frac{\sigma_o^2}{N_o}}}. \quad (11)$$

The described parametric mappings are exemplary only. The parametric map 62 can be constructed about essentially any image characteristic, such as the spin density (ρ) or the T1 decay time constant or rate, using any imaging and image processing methods that differentiate or emphasize the selected tissue conditions. Those skilled in the art can select appropriate conditions for parametric images 60 from which a selected parametric map 62 is constructed. For example, in yet another suitable embodiment the parametric map 62 is a diffusion image constructed from parametric images 60 taken with varying diffusion-inducing gradients. A diffusion map is suitable for detecting certain coronary diseases and other cardiac defects which are not adequately revealed by a T2* or T2 analysis. In still yet another contemplated parametric mapping, a biexponential regression method is employed rather than the described exemplary exponential regression method. As is known to the art, biexponential mapping can provide improved sensitivity and specificity to compromised tissues.

Although endogenous parametric mapping is described above, it is also contemplated to employ a magnetic contrast agent other than the magnetic contrast agent 54 (second magnetic contrast agent not shown) during the parametric mapping. The magnetic contrast agent used for the parametric mapping should be one which will not interfere with the subsequent FPM imaging employing the contrast agent 54. For example, a contrast agent which affects the magnetization in a different and distinguishable manner from the contrast agent 54 is suitable for use as the optional second contrast agent.

Based at least on the parametric map 62, piloting information 64 is obtained. The piloting information 64 typically includes parameters such as an optimized slice position and orientation, an imaging volume of interest, a number of slices, a spacing of slices, a slice thickness, a field of view, direction cosines, and an optimized level of stress (e.g., a minimum stress level sufficient to image a cardiac defect). Of course, other piloting information can also be extracted.

Optionally, the piloting information 64 is extracted from the parametric map 62 in combination with one or more of the parametric images 60. For example, the parametric map 62 can be additively combined with one of the parametric images 60 to provide context for the parametric map. Portions of the parametric map 62 which are not of interest, such as air pockets, can be masked using one of the parametric images 60.

The piloting information 64 is extracted manually, or using automated thresholding, or by other types of image analysis. The extracted piloting 64 is input to the sequence control processor 34 for use in optimizing first pass method (FPM) imaging and/or late enhancement imaging in the presence of the administered contrast agent 54. Because the piloting information 64 is used, the time-critical FPM imaging is not performed indiscriminately, but rather is focused on one or more defects indicated by the piloting. Since critical FPM imaging time is not being used to locate heart defects or to select optimized imaging conditions, the brief time window available for FPM imaging is effectively used to obtain selected, highly detailed information about the known defect or defects.

The reconstructed FPM or late enhancement images are stored in an FPM image memory 66. The reconstructed parametric images 60, parametric map 62, FPM or delayed enhancement 66 images are selectively input to a display processor 68 for formatting to be displayed on a user interface 70, which typically includes a color monitor, high resolution printer, animation workstation, or similar graphical display device. Optionally, a fused image constructed from the parametric map 62 and one or more FPM images 66 is displayed.

The user interface 70 provides interfacing with an associated user 72, who can program the sequence control processor 34, select images to view, and the like. The user 72 identifies regions of the heart that appear abnormal based at least on information contained in the parametric map 62, and selects the orientation and position of slices that optimally image all or a substantial part of the damaged or potentially damaged tissue. In a suitable embodiment, the user interface 70 is a computer workstation or personal computer that optionally includes access to a computer network and/or the Internet, and that optionally also physically embodies other selected system elements such as the memories 36, 60, 62, 66, the reconstruction processor 38, et cetera.

Figure 2:
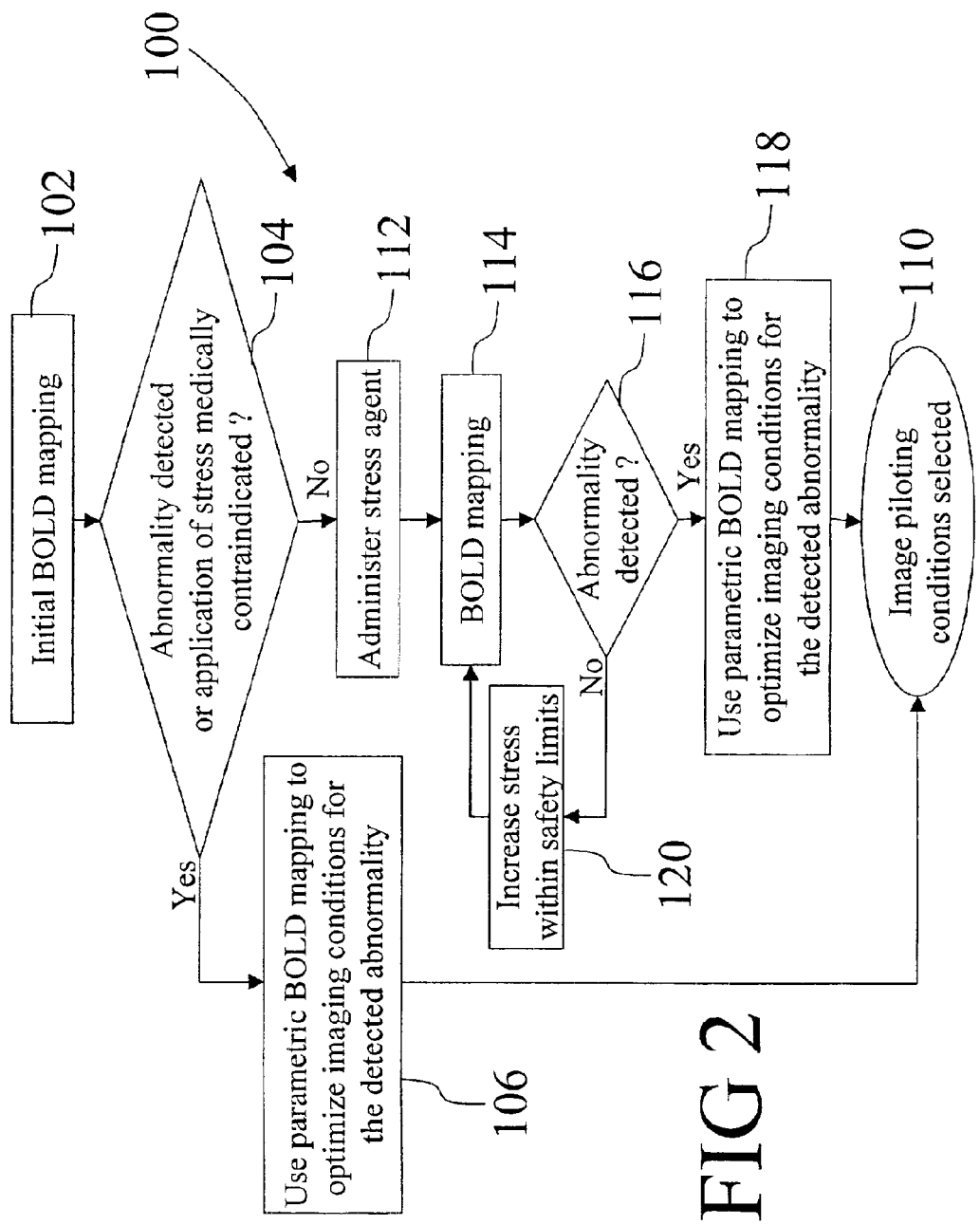
FIG. 2 is a flow chart of an exemplary method for obtaining piloting information using parametric imaging employing the BOLD contrast mechanism.

With continuing reference to FIG. 1 and with further reference to FIG. 2, a suitable embodiment of a method 100 for obtaining the piloting information 64 is described. In the exemplary method 100, T2* parametric maps of the cardiac region are acquired in a cardiac-segmented multiple-echo sequence. Of course, other types of parametric maps can also be employed, such as T2 maps, diffusion (D) maps, spin density (ρ) maps, T1 maps, or the like. Parametric T2* maps advantageously show strong blood oxygenation level dependence (BOLD) contrast, and are therefore particularly suitable for identifying poorly oxygenated cardiac tissue which is often associated with coronary diseases and for generating appropriate piloting information for imaging such tissue by a subsequent first-pass method (FPM).

In the method 100, an initial parametric T2* or BOLD mapping 102 is optionally performed on the patient without administering the stress agent 56. In a suitable embodiment, the BOLD mapping 102 entails obtaining a plurality of parametric images with varying echo times and correspondingly varying T2* weightings, and extracting the T2* decay time constant or corresponding T2* decay rate in pixel-wise fashion to construct the T2* map including BOLD contrast (steps not shown). The parametric images are optionally taken responsive to a single RF excitation pulse using multiple echo imaging. Exemplary imaging parameters for the BOLD cardiac mapping 102 include TE=2.2 ms, BW=125 kHz/pixel, FOV=39 cm, PSR=1.0, a 128×128 matrix, 10 mm thickness, and a PEG size of 8 to 16, with eight echoes acquired per RF excitation over four seconds. Of course, those skilled in the art can tailor the imaging conditions of the parametric mapping 102 for specific clinical applications.

The BOLD mapping 102 typically includes acquisition of a few slices, e.g. six axially oriented slices. In a decision step 104, if defects or heart abnormalities are detected in the mapping 102, or if a medical contraindication to application of a stress agent exists, parametric BOLD mapping without stress is used to optimize 106 the imaging conditions for the detected abnormality. The optimizing 106 typically includes optimizing the image slices' position and orientation, the field of view, the direction cosines, the number of slices, slice thicknesses, and et cetera. For example, an optimized slice orientation, which is in general non-axially oriented, is identified. The optimized slice selections can be unevenly spaced, or even non-parallel. The optimization 106 selects image piloting conditions 110 for use in later contrast-enhanced cardiac imaging of a transient distribution of the contrast agent in the heart.

The BOLD mapping 102 in the absence of artificially induced stress or metabolic elevation usually has a weak contrast for poorly oxygenated cardiac tissue, because at rest the cardiac tissue requires only a minimal throughput of oxygenated blood which a partially blocked blood vessel may be able to satisfy. The T2* BOLD contrast signal has been observed to increase by as much as 47% in response to an administered pharmacological stress agent, due to higher demand for oxygenated blood by heart tissues under stressed conditions.

Hence, if at the decision step 104 no abnormality is detected in BOLD parametric mapping 102, without stress, or if an abnormality is detected but has unacceptably weak image contrast, and if no medical contraindication to the application of a stress agent 56 exists, then the stress agent 56 is optionally administered 112 to raise the metabolism of the patient and increase the oxygen demands of the cardiac tissue. In a suitable embodiment, the stress agent 56 is applied to increase the heart pulse rate to a selected level, such as 120 heart beats per minute. Alternatively, physical stress is applied, e.g. the patient runs on a treadmill to raise his or her pulse. However, the use of chemical stress agents is generally more controllable, can be administered with the patient 18 in the scanner bore, and is preferred.

Of course, other types of enhancing agents besides stress agents can be employed to improve the parametric map contrast. The selected enhancing agent should be one which does not interfere with the contrast agent 54 employed in the transient distribution image (to be discussed later with reference to FIG. 3), or which induces a rapid and transient effect, so that the enhancing agent does not interfere with the subsequent contrast-enhanced transient imaging.

In cases where stress would adversely affect the subsequent contrast enhanced clinical imaging, or where the patient's medical condition contraindicates administering a stress agent, application 112 of the stress agent 56 is optionally omitted, and piloting is performed using BOLD parametric mapping 106 obtained with the patient 18 unstressed.

Once the stress agent 56 is administered 112, T2* BOLD parametric mapping 114 is performed under the stressed conditions. If a heart abnormality is detected 116, the BOLD mapping under stress is used to optimize 118 the imaging conditions for the detected abnormality. The optimization 118 typically includes optimizing the image slices' position and orientation, field of view, direction cosines, number and thickness of slices, and the like. The optimization 118 selects the image piloting conditions 110 for use in later contrast-enhanced cardiac imaging of a transient contrast agent distribution in the heart.

With continuing reference to FIGS. 1 and 2, if no heart abnormalities of interest are detected 116 using the BOLD imaging 114 under stress, or if the image contrast for detected abnormalities is unsatisfactory, the stress level is optionally increased 120 by increasing the stress agent 56 dosage within safety limits and repeating the BOLD mapping 114 at the higher stress level. Those skilled in the art will recognize that the types of chemical stress agents typically used for medical imaging, such as dobutamine, dipyridamole, and adenosine, produce rapid physiological responses similar to an adrenaline rush, and so patient 18 stress levels are controllably and rapidly modulated using such chemical agents to effectuate efficient acquisition of piloting information 110 using the method 100.

Figure 3:
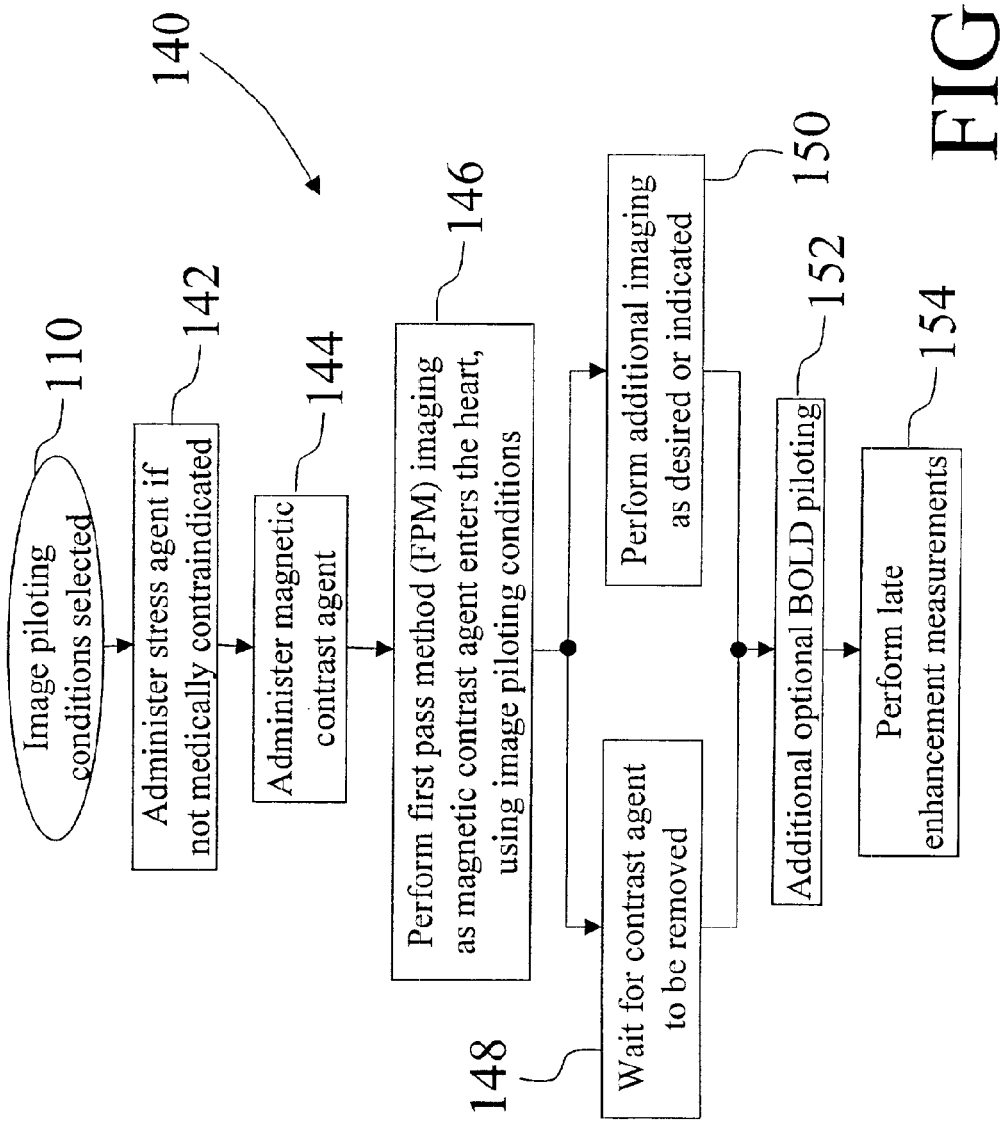
FIG. 3 is a flow chart of an exemplary method for obtaining first pass method (FPM) images and late enhancement images using piloting information obtained from BOLD piloting.

With continuing reference to FIGS. 1 and 2 and with further reference to FIG. 3, once the piloting conditions 110 have been selected according to the method 100, contrast-enhanced first pass method (FPM) imaging and/or late enhancement imaging is implemented according to an exemplary method 140. If the FPM imaging is to be performed under stressed conditions as indicated by the piloting information 110, and if there is no medical contraindication to administering the stress agent 56, an appropriate dosage of the stress agent 56 is administered in a step 142. If, however, cardiac abnormalities are projected based on the piloting information 110 to be adequately imaged without chemically induced stress, or if the administering of the stress agent 56 is medically contraindicated, the administering of the stress agent 142 is optionally omitted.

The contrast agent 54 is administered in a step 144. In a suitable embodiment the contrast agent 54 is an administered bolus injection of a gadolinium (Gd) chelate magnetic contrast agent which is known in the art. The Gd rapidly moves through the blood stream including the coronary vessels and is absorbed by the heart tissues through capillary blood vessels, perfusion, or other mechanisms. Those skilled in the art know that Gd absorption into coronary tissues occurs over a very short time frame on the order of seconds, leaving the diagnostician or other MRI operator little margin for error in the selection of FPM imaging slices and conditions. Furthermore, repetition of the FPM imaging using successive bolus injections is undesirable due to possible contamination of the later FPM images by residual Gd from previous bolus injections.

In the improved exemplary method 100, 140 described herein, the image piloting conditions 110 obtained from T2* BOLD image mapping are used to select optimized FPM imaging conditions, e.g. slice number, slice thickness, slice position, slice orientation, field of view, and the like, which are used in performing optimized FPM imaging 146. For example, non-axial or even non-parallel slices can be selected based on the piloting information 110. The limited FPM acquisition time window, during which a transient contrast agent distribution is present in the cardiac tissues, is optimally used for imaging cardiac defects previously identified by the piloting method 100. The likelihood of missing a damaged cardiac region during FPM imaging is minimized.

In the method 140, the FPM imaging step 146 typically includes acquiring a few (e.g., four or five) well-placed and well-oriented FPM image slices whose placement and orientation is based on the piloting 110. Since the slice selection and placement is determined a priori based on the piloting 110, the limited time available for FPM imaging 146 is optimally used to obtain higher image resolution in both the slice plane and in the slice-select gradient direction (through the use of more closely spaced or thinner slices).

In one suitable embodiment, T1-weighted FPM images are acquired. Because the piloting information 110 is available, it is not necessary to use the limited imaging time to maximally cover the cardiac tissue. Instead, time-intensive cardiac segmented gating is optionally employed to acquire higher resolution images with reduced cardiac motion blurring in the area of a priori identified defects.

Once the Gd agent has been substantially absorbed into both the healthy cardiac tissue and the blood flow impaired or dead tissue, i.e. a few seconds after administering 144 the contrast agent 54, the temporal window for FPM imaging 146 has passed. Additional information is optionally obtained by imaging cardiac tissue during the period following the essential completion of influx of the contrast agent into the cardiac tissue, in a technique known as late enhancement.

To obtain late enhancement imaging, the operator 72 and the patient 18 delay 148 until the Gd is substantially removed from the body via the kidneys, except for residual Gd in those areas of the cardiac or other organ tissue which are in poor communication with the vasculature. During this waiting time 148, which can range from tens of minutes to hours, additional imaging 150 is optionally periodically performed to monitor the removal of Gd and to predict optimal timing for the late enhancement imaging, or for clinical imaging other than the FPM or late enhancement imaging.

As the contrast agent 54 is being removed and a transient contrast agent distribution begins to appear in the cardiac tissues due to the Gd removal, an additional BOLD-based piloting step 152 is optionally performed substantially in accordance with the method 100 preparatory to the late enhancement imaging. In particular, because delayed enhancement is a weak contrast mechanism, the piloting step 152 preferably includes optimization of imaging parameters such as the time-to-echo and the flip angle. The BOLD piloting step 152 is also used to adjust for patient movement during the prolonged waiting period 148.

Based on information obtained by the piloting step 152, late enhancement imaging data acquisition sequences 154 are performed. Because of the weak late enhancement contrast and the relatively wide time window over which the late enhancement imaging sequences 154 can be performed, the imaging step 154 preferably includes a plurality of images acquired using different echo times and flip angles. Echo times and flip angles which are most likely to produce good delayed enhancement contrast are selected based on the piloting 152. Similarly, if initial late enhancement imaging 154 is unsatisfactory, e.g. because the temporal delay has been insufficient for optimal late enhancement, the piloting step 152 is optionally repeated prior to additional late enhancement imaging 154.

Those skilled in the art will recognize that the combined parametric mapping-FPM method 100, 140 provides substantial improvement over prior art methods for the assessment by MRI of coronary disease, tissue viability, and cardiac function. The combined parametric mapping-FPM method 100, 140 particularly takes advantage of the complementary strengths of BOLD contrast imaging and FPM to produce an improved clinical work flow which minimizes stress to the patient, makes optimally efficient use of limited clinical MRI time, and maximizes the probability of acquiring diagnostically useful cardiac MRI images.

With reference returning to FIGS. 1 and 2, in the method 100 the optimizing steps 106, 118 involve acquiring successive image slices having varying orientations and positions to iteratively identify an optimized slice position and orientation which best images a detected defect. The iterative optimizing 106, 118 is optionally performed manually as the user 72 acquires a parametric map of a slice, views the map, estimates based upon the current parametric map a new slice position and/or orientation, and repeats the acquiring, viewing, and estimating until the user 72 is satisfied that an optimized image orientation and position has been obtained. This approach has the disadvantage of being inexact and dependent upon the judgment of the user 72.

Figure 4:
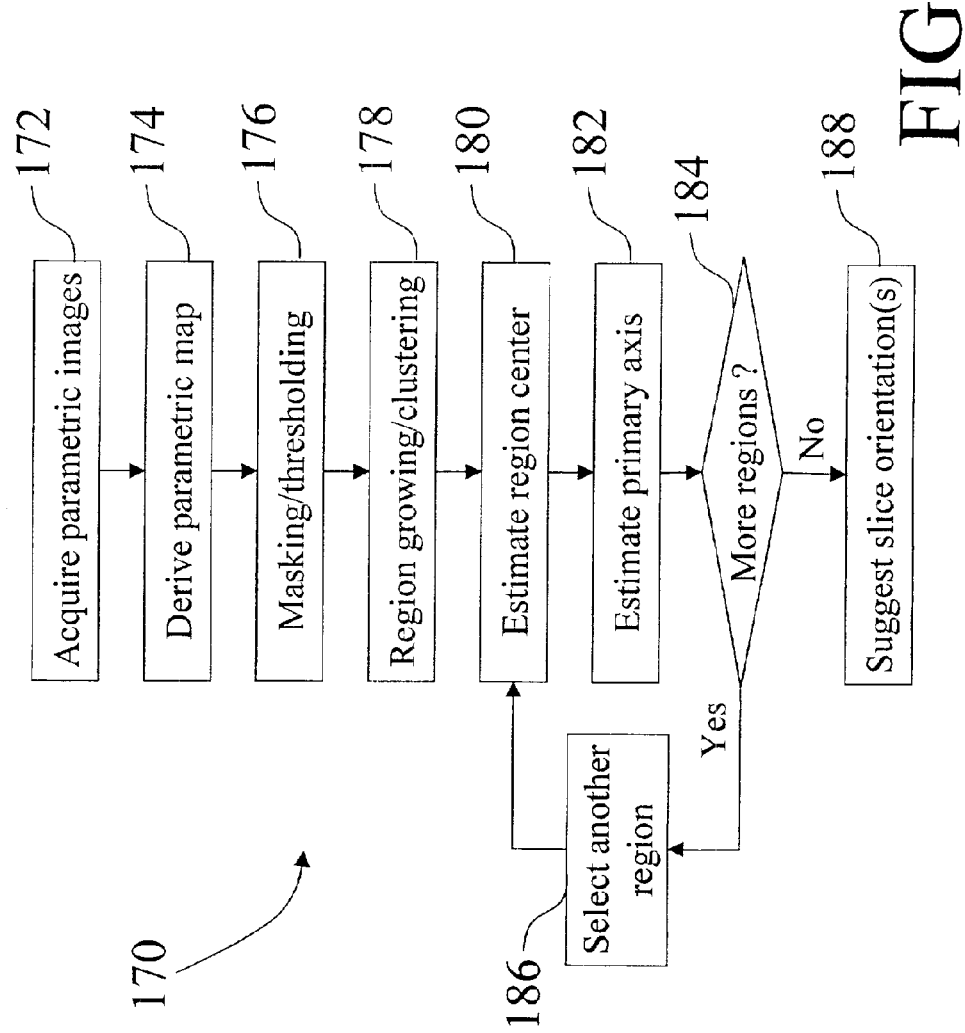
FIG. 4 is a flow chart of an exemplary method for automatically selecting an improved slice orientation and position for parametric mapping based on an existing parametric map.

With reference to FIG. 4, a method 170 for automatically selecting a next slice which is estimated to better image the defect is described. The current iteration of parametric images are acquired 172 using a current slice orientation and position, and a parametric map of that position and orientation is derived 174. Portions of the parametric map are masked or thresholded in a step 176 to improve contrast of the diseased or damaged tissue. In a suitable embodiment, the parametric map, or portions thereof, are masked using a corresponding cardiac image to make the diseased tissue more apparent, followed by a multi-level thresholding which identifies pixels corresponding to damaged tissue. The identified regions corresponding to damaged tissue are processed using a growing or clustering technique in a step 178 to determine distinct image regions corresponding to unhealthy cardiac tissue.

In a suitable method, two regions $R_i$ and $R_j$ have corresponding perimeters $P_i$ and $P_j$. There is a common boundary of length L including a number w of ambiguous boundary pixels which are not clearly within either region and which possibly form a connection between the regions. The regions $R_i$ and $R_j$ are combined if they meet one or more of the following criteria:

$$\frac{w}{\min\{P_i, P_j\}} > T_a \text{ or } \frac{W}{L} > T_b \text{ or } S < T_c, \quad (12)$$

where S represents the calculated similarity distance between regions $R_i$ and $R_j$. S is calculated using one of several known techniques such as the dot product, similarity rule, weighted Euclidean distance, and normalized correlation. The threshold $T_a$ controls the size of the region to be merged. Larger $T_a$ values (limited by $T_a<1$) require larger size differences between the regions $R_i$ and $R_j$ in order to merge the smaller region into the larger one. The threshold $T_b$ represents the strength of the boundary. The threshold $T_c$ represents a threshold similarity difference.

The region center is determined in a step 180. In one suitable embodiment, the center of mass is found using known mechanical principles. For a region R with N pixels, where i and j represent the components of the pixel value at a given location, the quantities:

$$i_o = \frac{1}{N}\sum\sum_{(i,j)\in R} i, \quad j_o = \frac{1}{N}\sum\sum_{(i,j)\in R} j, \quad (13)$$

are defined, where $(i_o, j_o)$ represents the center of mass (or signal intensity) for the region.

With continuing reference to FIG. 4, in another suitable method for the step 180 of determining the region center, a weighted peak is found using the method of converging squares known to the art. An initial square analysis region of dimension (d×d) substantially encompassing the region R is divided into four square test regions each of dimension ((d−1)×(d−1)). The mean pixel intensity of each of the four square test regions is computed, and the test region having the largest mean pixel intensity is selected for continued analysis. The process is iteratively repeated with each iteration producing an analysis region dimensionally reduced by one pixel in each coordinate direction, until a 2×2 analysis region remains. That pixel among the four remaining pixels having the highest intensity is selected as the weighted peak.

With continuing reference to FIG. 4, the primary axis of the slice to be selected is identified in a step 182. The primary axis passes through the region center identified in the step 180. In a suitable embodiment, the primary axis is determined using the least moment of inertia method. The (p,q) order central moments $\mu_{p,q}$ for the region R are calculated as:

$$\mu_{p,q} = \sum\sum_{(i,j)\in R}(i-i_o)^p(j-j_o)^q, \qquad (14)$$

where $i_o$ and $j_o$ are given in equation (13). The angle θ corresponding to the axis of the least moment of inertia specifies the optimal orientation. The moment of inertia as a function of angle θ is given by:

$$I(\theta) = \sum\sum_{(i,j)\in R}[(j-j_o)\cos\theta - (i-i_o)\sin\theta]^2. \qquad (15)$$

Minimizing I(θ) with respect to θ results in the optimized angle $\theta_{opt}$ of the axis of the least moment of inertia:

$$\theta_{opt} = \frac{1}{2}\tan^{-1}\left[\frac{2\mu_{1,1}}{\mu_{2,0}-\mu_{0,2}}\right]. \qquad (16)$$

Expanding equation (16) gives:

$$\theta_{opt} = \frac{1}{2}\tan^{-1}\left[\frac{2\sum\sum_{(i,j)\in R}(i-i_o)(j-j_o)}{\left[\sum\sum_{(i,j)\in R}(i-i_o)^2\right]-\left[\sum\sum_{(i,j)\in R}(j-j_o)^2\right]}\right]. \qquad (17)$$

The primary axis is a line passing through the region center (found in the step 180) oriented at an angle $\theta_{opt}$ (found in the step 182). A suggested slice for imaging is identified as a slice oriented such that it contains the region center and is normal to the primary axis. The suggested slice thickness is typically unchanged from the thickness of the previous slice, but other thicknesses can also be used.

With continuing reference to FIG. 4, the steps 180, 182 identify a primary axis for a region. If a plurality of regions are identified by the masking/thresholding 176 and the region growing/clustering 178, then at a decision step 184 the method 170 selects another region 186 and the steps 180, 182 are repeated to identify a primary axis for the next region. After all the identified regions are processed, the method 170 provides one or more suggested slice orientations in a step 188. Alternatively, after the region growing/clustering step 178, the user is prompted to select a region whose primary axis is to be identified according to the steps 180, 182, and the repetitive looping steps 184, 186 are optionally omitted. In either case, once a suggested slice is accepted by the user (step not shown), the parametric imaging and mapping is repeated on the suggested slice to verify the improved slice position and orientation for imaging the defect. The process 170 is optionally repeated until the user 72 is satisfied that an optimized slice position and orientation has been identified.

Those skilled in the art will recognize that the apparatus and method described herein are not limited in application to the heart, but rather are applicable to essentially any organ for which imaging assessment of tissue viability is desirable. Other organs for which the method is contemplated as being particularly suitable include the kidney, brain, and liver.

The apparatus and method are also suitable for use in conjunction with imaging navigation and image nagivating methods known to the art. In a typical navigator, MRI imaging is used to monitor a patient movement, such as diaphragm movement tracking, to effectuate image registration during a prolonged imaging session. Similarly, for cardiac imaging the apparatus and method are suitable for use in conjunction with cardiac segmented-gated imaging techniques known to the art.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for imaging tissue viability or vascular function in a patient using a magnetic resonance imaging (MRI) apparatus, the method comprising:

acquiring a parametric map having blood oxygenation level dependent contrast;

estimating an improved slice orientation based on the parametric map;

optimizing the slice orientation using at least one iteration of the acquiring and estimating;

subsequent to the acquiring and optimizing, administering a magnetic contrast agent to the patient; and imaging during a transient distribution of the contrast agent in the patient at the optimized slice orientation.

2. The method as set forth in claim 1, further including:

administering a stress-causing agent to the patient to alter patient metabolism during the acquiring of the parametric map.

3. The method as set forth in claim 2, wherein the stress-causing agent includes at least one of dobutamine, dipyridamole, and adenosine.

4. The method as set forth in claim 1, wherein the step of imaging a transient distribution of the contrast agent in the patient includes:

acquiring first pass image data during a time when the contrast agent is taken up into an organ of interest to be imaged.

5. The method as set forth in claim 1, wherein the step of imaging a transient distribution of the contrast agent in the patient includes:

acquiring late enhancement image data during a time when the contrast agent is removed from an organ of interest.

6. The method as set forth in claim 1, wherein the step of imaging a transient distribution of the contrast agent in the patient further includes:

delaying imaging for a selected time;

subsequent to the imaging delay, acquiring a plurality of delayed parametric images; and deriving a parametric map having a late enhancement contrast from the delayed parametric images.

7. The method as set forth in claim 1, wherein the acquiring of a parametric map includes:

acquiring a plurality of images having a varying T2* or T2 weighting; and constructing a T2* or T2 map from the plurality of images.

8. The method as set forth in claim 1, wherein the acquiring of a parametric map includes:
acquiring a plurality of images during a multiple-echo readout; and
estimating a pixel intensity decay time constant or rate for each pixel based on the plurality of images.

9. The method as set forth in claim 1, wherein the acquiring of a parametric map includes:
administering a stress agent to the patient;
prior to the administering of the stress agent, acquiring a first set of images;
subsequent to the administering of the stress agent, acquiring a second set of images; and
combining the first and second sets of images to construct a parametric map identifying stressed tissues.

10. The method as set forth in claim 9, wherein the combining of the first and second sets of images includes:
calculating at least one unstressed statistical quantity for each pixel of the first set of images;
calculating at least one stressed statistical quantity for each pixel of the second set of images; and
combining the stressed and unstressed statistical quantities to form a parametric map indicative of a statistical intensity change due to the administering of the stress agent.

11. method for imaging tissue viability or vascular function in a patient using a magnetic resonance imaging (MRI) apparatus, the method comprising:
acquiring a parametric map having blood oxygenation level dependent contrast;
determining piloting information including at least a selected slice orientation based on the blood oxygenation contrast of the parametric map;
subsequent to the acquiring, administering a magnetic contrast agent to the patient; and
imaging during a transient distribution of the contrast agent in the patient using imaging parameters based on the piloting information;
wherein the parametric map and the transient distribution image are of at least a portion of the patient's heart.

12. A method for imaging tissue viability or vascular function in a patient using a magnetic resonance imaging (MRI) apparatus, the method comprising:
(a) acquiring a plurality of images during a multiple-echo readout;
(b) estimating a pixel intensity decay time constant or rate for each pixel based on the plurality of images;
(c) constructing a first parametric map based on the intensity decay time constants or rates of the pixels;
(d) identifying an object of interest in the first parametric map;
(e) locating a center of the identified object;
(f) estimating a primary axis extending from the located center of the identified object; and
(g) repeating the steps (a)–(c) to construct an improved parametric map corresponding to the located center and the estimated primary axis,
(h) determining piloting information including at least a selected slice orientation based on the blood oxygenation contrast of the parametric map;
(i) subsequent to the acquiring (a), administering a magnetic contrast agent to the patient; and (j) imaging during a transient distribution of the contrast agent in the patient using imaging parameters based on the piloting information.

13. A method for assessing tissue in a patient using a magnetic resonance imaging (MRI) apparatus, the method comprising:
acquiring a plurality of parametric images with at least one varying imaging parameter;
constructing a parametric map incorporating a diffusion weighted image from the plurality of parametric images;
from at least the parametric map, identifying at least one pilot parameter including at least a volume of interest for a diagnostic image;
subsequent to the acquiring, administering a contrast agent to the patient; and
imaging the identified volume of interest during influx of the administered contrast agent into the identified volume of interest, the imaging using the at least one identified pilot parameter.

14. The method as set forth in claim 13, wherein the parametric map includes a map indicative of stress-induced image contrast change or a map of pixel intensity decay time constants or rates.

15. The method as set forth in claim 13, further including:
subsequent to the step of imaging the volume of interest, acquiring late enhancement image data during a time period when the contrast agent leaves the volume of interest.

16. The method as set forth in claim 13, wherein at least one of the step of acquiring a plurality of parametric images and the step of imaging the identified volume of interest includes:
coordinating the acquiring or the imaging with cardiac gating or image navigation.

17. The method as set forth in claim 13, wherein the volume of interest includes at least a portion of one of a heart, a kidney, a brain, and a liver.

18. The method as set forth in claim 13, wherein the pilot parameters further include at least one of a direction cosine, a slice position, a field of view, and a slice thickness.

19. The method as set forth in claim 13, further including:
based on the parametric map, estimating an improved slice orientation; and
repeating the acquiring and constructing steps at the improved slice orientation.

20. The method as set forth in claim 13, wherein the administering of a contrast agent includes:
administering a contrast agent containing gadolinium.

21. The method as set forth in claim 13, wherein the step of acquiring a plurality of parametric images includes:
acquiring multiple-echo image data.

22. The method as set forth in claim 13, wherein the step of acquiring a plurality of parametric images includes:
before or during the acquiring of a plurality of parametric images, administering an enhancing agent to the patient that enhances a selected contrast of the parametric map.

23. A method for assessing tissue in a patient using a magnetic resonance imaging (MRI) apparatus, the method comprising:
acquiring a plurality of parametric images with at least one varying imaging parameter;
constructing a parametric map from the plurality of parametric images;
identifying at least one pilot parameter including at least a volume of interest for a diagnostic image based on the parametric map;

subsequent to the acquiring, administering a magnetic contrast agent to the patient;

before or during the acquiring of a plurality of parametric images, administering a second magnetic contrast agent to the patient, the second magnetic contrast agent affecting tissue magnetization in a different and distinguishable manner from the contrast agent, the second contrast agent providing parametric image contrast; and imaging the identified volume of interest during influx of the administered contrast agent into the identified volume of interest, the imaging using the at least one identified pilot parameter.

24. The method as set forth in claim 23, wherein the step of identifying at least one pilot parameter includes:

combining at least one parametric image and the parametric map to form a new image; and identifying the at least one pilot parameter based on the new image.

25. A method for assessing tissue in a patient using a magnetic resonance imaging (MRI) apparatus, the method comprising:

acquiring a plurality of parametric images with at least one varying imaging parameter;

constructing a parametric map from the plurality of parametric images;

from at least the parametric map, identifying at least one pilot parameter including at least a volume of interest for a diagnostic image;

based on the parametric map, estimating an improved slice orientation by identifying an object of interest in the parametric map, locating a center of the identified object, and estimating a primary axis extending from the located center of the identified object;

repeating the acquiring and constructing steps at the improved slice orientation;

subsequent to the acquiring, administering a contrast agent to the patient; and imaging the identified volume of interest during influx of the administered contrast agent into the identified volume of interest, the imaging using the at least one identified pilot parameter.

26. An apparatus for characterizing contrast agent uptake in a patient, the apparatus comprising:

a means for exciting a selected magnetic resonance in the patient;

a means for detecting radio-frequency resonance signals emanating from the patient responsive to the exciting of the selected magnetic resonance;

a means for reconstructing image representations from the detected radio-frequency resonance signals; and a means for controlling the exciting means, the detecting means, and the reconstructing means, the means for controlling implementing the steps of:

acquiring a plurality of images of a region of interest in the patient wherein the plurality of images parametrically depend upon at least one imaging parameter, constructing a parametric map based on the plurality of images, determining optimized imaging conditions based on at least the parametric map, and first-pass imaging during an uptake of an administered contrast agent into the region of interest based on the optimized conditions wherein the first-pass imaging includes contrast due to the administered contrast agent.

27. The apparatus as set forth in claim 26, wherein the constructing of a parametric map includes:

obtaining a pixel intensity decay time constant or rate by regression analysis for a pixel of the plurality of images, which plurality of images have varying echo times; and repeating the regression analysis for each pixel to generate a map of pixel intensity decay time constants or rates.

28. The apparatus as set forth in claim 26, wherein the constructing of a parametric map includes:

estimating a statistical pixel intensity change between a first portion of the plurality of images acquired prior to an administering of a stress agent and a second portion of the plurality of images acquired subsequent to the administering of the stress agent; and repeating the statistical estimating for each pixel to generate a map of stress-induced magnetization change.

* * * * *